Figure 1:
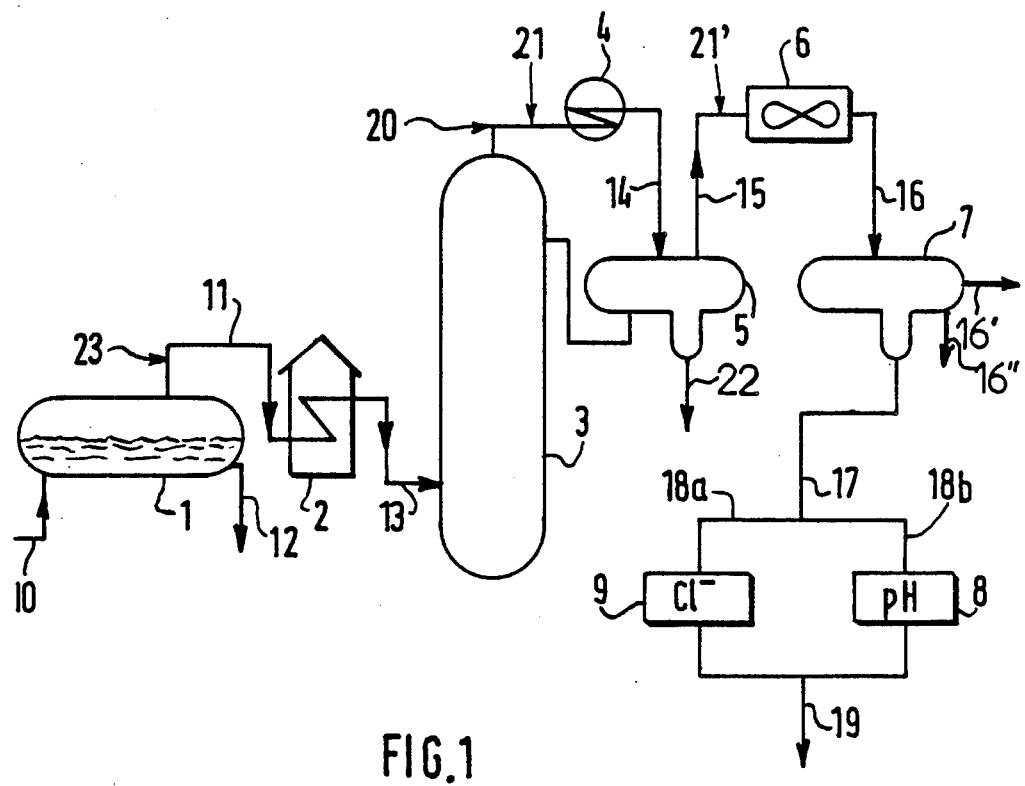

United States Patent [19]
Pauly et al.

[11] Patent Number: 4,942,133
[45] Date of Patent: Jul. 17, 1990

[54] PROCEDURE FOR THE CONTINUOUS ANALYSIS OF THE CHLORIDE IONS PRESENT IN THE OVERHEAD WATERS OF A HYDROCARBON DISTILLATION COLUMN

[75] Inventors: Jean-Francois Pauly, Le Havre; Gerard Roussel, Goderville, both of France

[73] Assignee: Compagnie de Raffinage et de Distribution, Perret, France

[21] Appl. No.: 288,026

[22] Filed: Dec. 21, 1988

[30] Foreign Application Priority Data

Dec. 21, 1987 [FR] France ................. 87 17821

[51] Int. Cl.⁵ ......................................... G01N 27/26
[52] U.S. Cl. ............................ 436/125; 204/153.13; 436/55; 436/60; 436/124; 436/149; 436/150; 436/151; 436/163; 436/175; 436/177; 436/178
[58] Field of Search ............... 436/124, 125, 149, 150, 436/151, 60, 55, 163, 175, 177, 178; 204/1 B, 419 IT

[56] References Cited

U.S. PATENT DOCUMENTS 4,581,134 4/1986 Richter, Jr. et al. ............. 210/96.1

FOREIGN PATENT DOCUMENTS 2292977 11/1975 France.
2342496 9/1977 France.
1201850 8/1970 United Kingdom.

OTHER PUBLICATIONS

Oil and Gas Journal, vol. 70, No. 29, 17 Jul. 1972, pp. 92–98; R-H. Hausler et al.: "Corrosion Controlled in Crude Units Overhead".
Erdöl Und Kohle, vol. 48, No. 2, Jun. 1975, pp. 227–282; J. Elster: "Overheadkorrosion in Rohöldestillations-anlagen".

Primary Examiner—Barry S. Richman
Assistant Examiner—Timothy M. McMahon
Attorney, Agent, or Firm—A. Thomas S. Safford

[57] ABSTRACT

Procedure and apparatus for the continuous analysis of the chloride ion content of overhead waters downstream of a hydrocarbon distillation column for more effectively preventing hydrochloric acid corrosion of downstream equipment while avoiding over-neutralizing the overhead waters to the detriment of the hydrocarbon product. This procedure comprises the following operations, in the order given or in a different order:
  Drawing from the overhead waters a stream of water for analysis;
  removing from the sample so drawn the hydrocarbons as well as the suspended matter;
  blowing nitrogen into the sample to sweep away the hydrogen sulfide ans the residual hydrocarbons;
  oxidizing the $S^{2-}$ or $HS^-$ sulfide ions to sulfate ions;
  acidifying the sample;
  finally, measuring by ionometry, and more particularly by means of a combined electrode, the content of chloride ions present.

16 Claims, 3 Drawing Sheets

PROCEDURE FOR THE CONTINUOUS ANALYSIS OF THE CHLORIDE IONS PRESENT IN THE OVERHEAD WATERS OF A HYDROCARBON DISTILLATION COLUMN

The present invention consists in a procedure for the continuous analysis of the chloride ions present in the overhead waters of a column for the distillation of hydrocarbons, and particularly of crude petroleums, or of atmospheric distillation residues. This invention further relates to an analyzer suitable for carrying out said analysis procedure.

It is known that the chloride ions present in the overhead waters of a column for the distillation of hydrocarbons, and particularly of crude petroleums, generally come from hydrolyzable salts initially contained in the hydrocarbons, which hydrolyze to form hydrochloric acid. This hydrochloric acid condenses in the cooling circuits located downstream of the top of the distillation tower and is the source of the corrosion observed in these circuits. These hydrolyzable salts are composed mainly of $MgCl_2$ and $CaCl_2$. To limit the quantity of these salts present in the hydrocarbons prior to distillation, it is the practice to desalt these hydrocarbons by means which are knwon per se and to inject soda after desalting to bring about the hydrolysis of these salts by replacing them with sodium chloride, which is then found in the distillation residues.

However, it is very difficult to adjust the quantity of soda to be injected, since maintaining a high rate of soda injection carries a penalty in that high sodium contents give rise to problems in the subsequenet treatment of the distillation residues, and particularly of the atmospheric and vacuum residues of a crude petroleum.

Furthermore, to neutralize the residual hydrochloric acid present in the vapors leaving the top of the distillation tower, it is known to inject at least ammonia and/or a corrosion inhibitor. The rate of ammonia injection depends on the measured pH of the overhead waters, which is maintained close to 6.

To adjust the rates of injection of soda or also of corrosion inhibitor, it is necessary to be able to monitor continuously the chloride content of the condensation waters in the overhead circuits, and to do so with as short a response time as possible.

In the case of the overhead waters in conventional atmospheric distillation, the analysis of the chloride ion content is at present performed discontinuously at time intervals spaced relatively far apart, on the order of once a day. This analysis is typically an argentometry (or, less frequently, an ionometry), usually performed in the control laboratory of the refinery on a sample, with the result reaching the operator only about 24 hours after the sampling. If the measurement has shown that the chloride ion content is higher than the desired value, the operator changes the rates of injection of soda and corrosion inhibitor; but this action does not have an immediate effect. If the time lag between the changing of the rate of soda injection after the desalter and its effect on the overhead waters is added to the delay in the analysis, it is apparent that the overhead circuit in conventional atmospheric distillation may be under conditions of severe corrosion for close to 30 hours.

Through measurements or evaluation of the rate of corrosion, the applicants have verified that when the chloride ion content of the overhead waters exceeds 10 ppm, very sharp acceleration of the corrosion of the overhead circuits is observed. Knowing this value (the chloride ion content) in real time therefore is an important parameter for: 1. Optimizing the rate of injection of soda and/or corrosion inhibitor;

2. increasing the service life of the overhead circuits and condensers;

3. upgrading the atmospheric residue and the fuel oils in view of the problems posed by the presence of sodium in the fuel oils.

To the best of applicants' knowledge, there is no procedure or apparatus in existence at present for carrying out a continuous analysis of the chloride ions present in overhead waters. In fact, it has not been possible to solve two technical problems:

The waters whose chloride ion content it is desired to measure also contain sulfur in the form of $S^{2-}$ and/or $HS^-$ sulfide ions. These interfere with the measurement of the chloride ions by causing substantial errors or deviations in the results. It should be borne in mind that the overhead waters in the atmospheric distillation of crude petroleum may contain from 0 to 400 ppm of $S^{2-}$ and/or $HS^-$ sulfide ions, depending on the nature of the crude.

During the operation of the distillation units, hydrocarbons may be entrained with the water, which will cause a gradual plugging of the sensitive portion of the electrode of the measuring cell when the measurement is made by ionometry, with the measurement rapidly becoming unreliable.

The present invention seeks to overcome the drawbacks outlined above, and to that end it teaches as a first embodiment, a procedure for the continuous analysis of the content of chloride ions present in the overhead waters of a hydrocarbon distillation column, said procedure being characterized by the following operations, in the order given or in a different order:

Drawing from the overhead waters a stream of water for analysis;

removing from the sample so drawn the hydrocarbons as well as the suspended matter;

blowing nitrogen into the resulting sampling to sweep away the hydrogen sulfide and the residual hydrocarbons;

oxidizing the sulfide ions to sulfate ions;

acidifying the sample;

finally, measuring by ionometry, and more particularly by means of a combined electrode in a measuring cell, the content of chloride ions present.

The procedure in accordance with the invention thus makes it possible to overcome the drawbacks due to the presence of hydrocarbons and $S^{2-}$ sulfide ions in the sample and, moreover, to avoid the drift of the signal of the combined electrode when the pH is greater than 7. In fact, sulfate ions do not interfere with this type of electrode, and the signal of this type of electrode is stable when the pH is maintained between 2 and 7.

As will be understood by one skilled in the after a review of the foregoing, the operation consisting of blowing nitrogen into the sampling for the purpose of sweeping away the hydrogen sulfide and the hydrocarbons may be performed upstream or downstream of the operations of oxidation and acidification of the sampling, since only the quantities of the sulfates stemming from the oxidation of a hydrogen sulfide will vary.

In a first aspect of the process invention, the hydrocarbons are removed from the sample of the overhead waters by filtering them out with an activated carbon filter.

In a second aspect, the sample of the overhead waters may be introduced into a vessel comprising at least one hydrocarbon detector and at least one discharge pipe, equipped with a valve or with valves electrically connected to the detector, permitting the sampling (i.e. a water portion of the sample) to flow to the measuring cell and also permitting the discharge of the sample when the hydrocarbons occupy too large a volume in the vessel.

For the detection of the presence of hydrocarbons in the sample, capacitive sensors, for example, a sensor marketed under the name Effector by IFM Electronic, or any other appropriate means may be used.

Detection of the hydrocarbons in said vessel has the advantage of reducing the risk of malfunctioning of the control of the water level in the overhead drum of the distillation unit, which may result in an excessive and unforeseeable discharge of hydrocarbons into the overhead-waters circuit of the distillation tower at certain moments.

Oxidation of the $S^{2-}$ and/or $HS^-$ sulfide ions to sulfate ions is accomplished by injection into the sampling, which has been freed of a large portion of the hydrocarbons, of a so-called oxidizing solution whose oxidizing power is sufficient, at the pH of the sampling, to oxidize the $S^{2-}$ and/or $HS^-$ sulfide ions to sulfate ions but not sufficient to transform the chloride ions into chlorate ions. This injection of the oxidizing solution is effected at such a pH that the formation of free sulfur that would tend to plug the sensitive portion of the measuring electrode or electrodes can be avoided.

That oxidizing power is a function of the respective potentials, at the pH of the sample, of the oxidation-reduction equilibria of the ion pairs present.

Thus, for oxidation of the sulfide ions to sulfate ions, the oxidizing solution may be selected from the group consisting of the bromates, $BrO_3^-$, the bichromates, $Cr_2O_7^{2-}$, the permanganates, $MnO_4^-$, the nitrates of alkali metals, alkaline-earth metals or other metals, and any other anion that is oxidizing for sulfide ions but nonoxidizing for chloride ions. The oxidizing ion concentration of the solution should range from 0.1M to 5M, and preferably from 0.5M to 3M.

In a first aspect of the invention, said oxidation should be carried out at a pH permitting the formation of free sulfur to be avoided by adding beforehand or simultaneously an alkaline agent so that the pH will be greater than 7; for example, a soda solution of a concentration which typically ranges from 0.5N to 2N. A preferred oxidizing solution of this first aspect of the invention consists of an aqueous solution of potassium permanganate and soda. In a second aspect, it is necessary to add simultaneously or subsequently an acidifying agent to the sampling so as to increase the oxidizing power of the oxidizing solution introduced. It is within the scope of the invention to introduce into the sampling in a single step an agent which simultaneously permits the oxidizing power of the oxidizing solution to be increased and the sampling to be acidified. A preferred oxidizing solution of this second aspect is a concentrated aqueous solution of sodium bromate ($NaBrO_3$).

The subsequent acidification of the sample to a pH ranging from 2 to 7 for the purpose of stabilizing the response of the electrode is accomplished by injection of an acid solution of a concentration of from 0.1 to 5N, and preferably from 0.5 to 2N, of at least one strong acid selected from the group consisting of sulfuric acid, nitric acid and te halogen acids, with the exception of hydrochloric acid.

Another embodiment of the invention relates to the analyzer for carrying out said procedure, which is characterized in that such apparatus comprises:

A device for the removal of the hydrocarbons, through which a portion of the overhead water drawn from the last overhead drum passes;

a pneumatic or electric proportioning pump which recovers a sampling of the water at the outlet of the hydrocarbon-removal device;

a holding tank provided at its base with a nitrogen source adapted to blow nitrogen into the sampling, and at its top with a membrane permeable to nitrogen and to volatile compounds, particularly hydrogen sulfide, $H_2S$, and optionally to the residual volatile hydrocarbons which are entrained by the nitrogen so blown in;

two injection devices for a first, oxidizing solution and a second, acidifying solution, respectively, each comprising a proportioning pump and a vessel containing said solution;

a measuring cell consisting of a closed electrolytic vessel equipped with a specific combined electrode for measuring the chloride ion concentration of the sampling flowing through said vessel, for example, a combined electrode of the CE 9417 B type, marketed by the Orion Company; and the associated electronic unit, connected to the electrode, which gives, in any appropriate form, the content of chloride ions present in the water.

The specific combined electrode is standardized in the usual manner with the aid of standard solutions representative of the overhead water after treatment (oxidation and acidification) and containing ammonium chloride which has been added in different concentrations.

In a first aspect of the hydrocarbon-removal device, the latter may consist of an activated carbon filter.

In a second aspect, which is preferred since it makes it possible to react more effectively to spurts of hydrocarbons in the waters collected from the last overhead drum, the removal device consists of a vessel equipped with a hydrocarbon level detector, preferably a commercial type of capacitive sensor. Said vessel further comprises a first outlet circuit, located in the upper portion of the vessel, permitting the removal of the hydrocarbons, and a second circuit, located in its lower portion, conducting the sampling of water without hydrocarbons to the measuring cell. These circuits are advantageously equipped with a valve or with valves whose actuation is controlled by the hydrocarbon level detector so as to interrupt the flow of the sample to the measuring cell when the volume of hydrocarbons in the vessel is too great and there is the risk of hydrocarbons susceptible of altering the response of the combined electrode being swept through the second circuit toward the measuring cell. One skilled in the art might advantageously dispense with the valve located in the second outlet circuit of the vessel and use the proportioning pump located downstream to interrupt the flow of liquid from the vessel.

Any analyzer to be set up on an industrial site should provide assurances of safety, and these requirements should be met by the analyzer in accordance with the invention, too. It is characterized in that all of its component parts are enclosed in a safety housing, which is preferably explosion proof when used in a refinery.

The invention will now be described with reference to the accompanying drawings, which are nonlimitative and in which—

Figure 2:
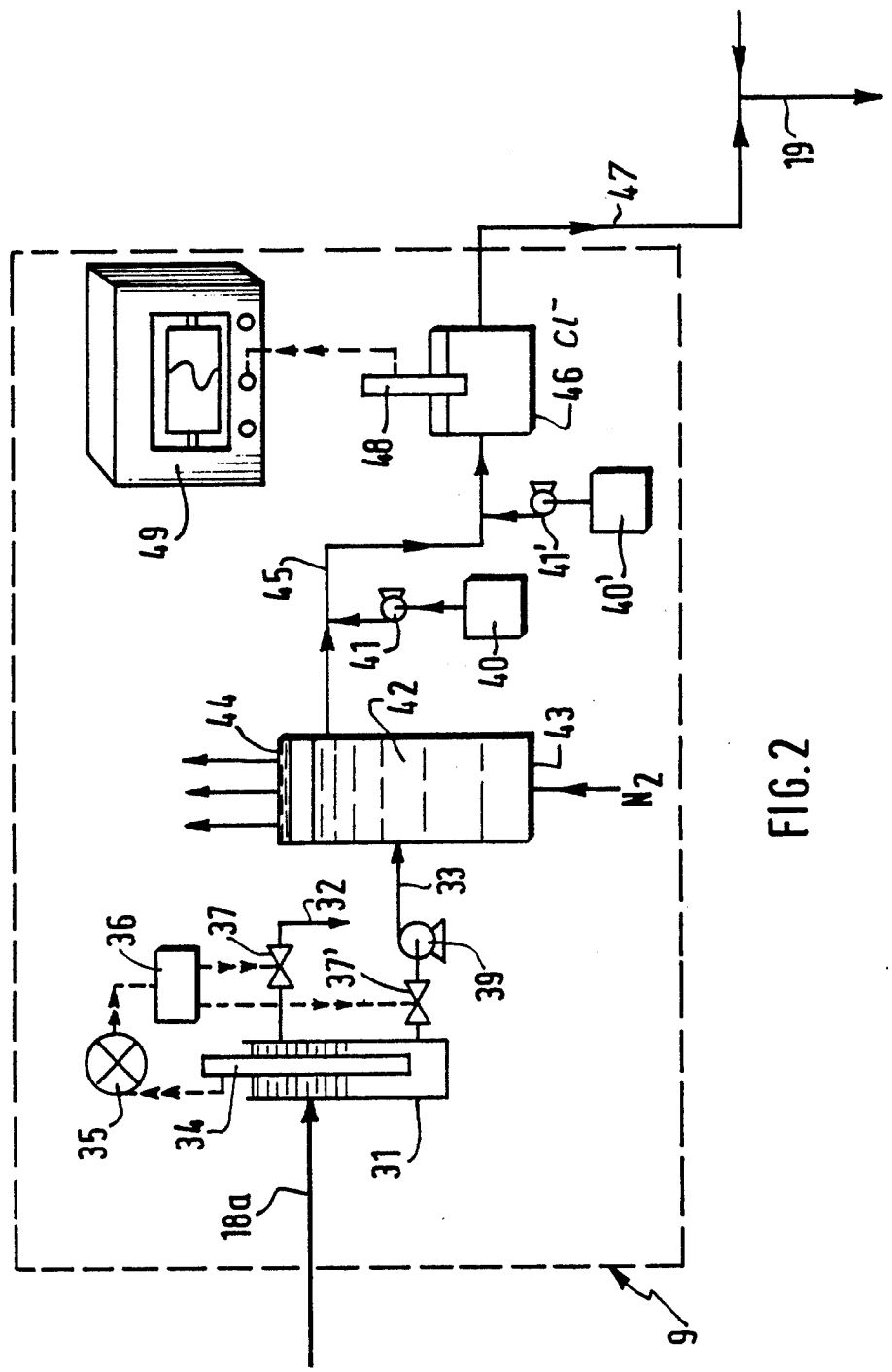
Figure 3:
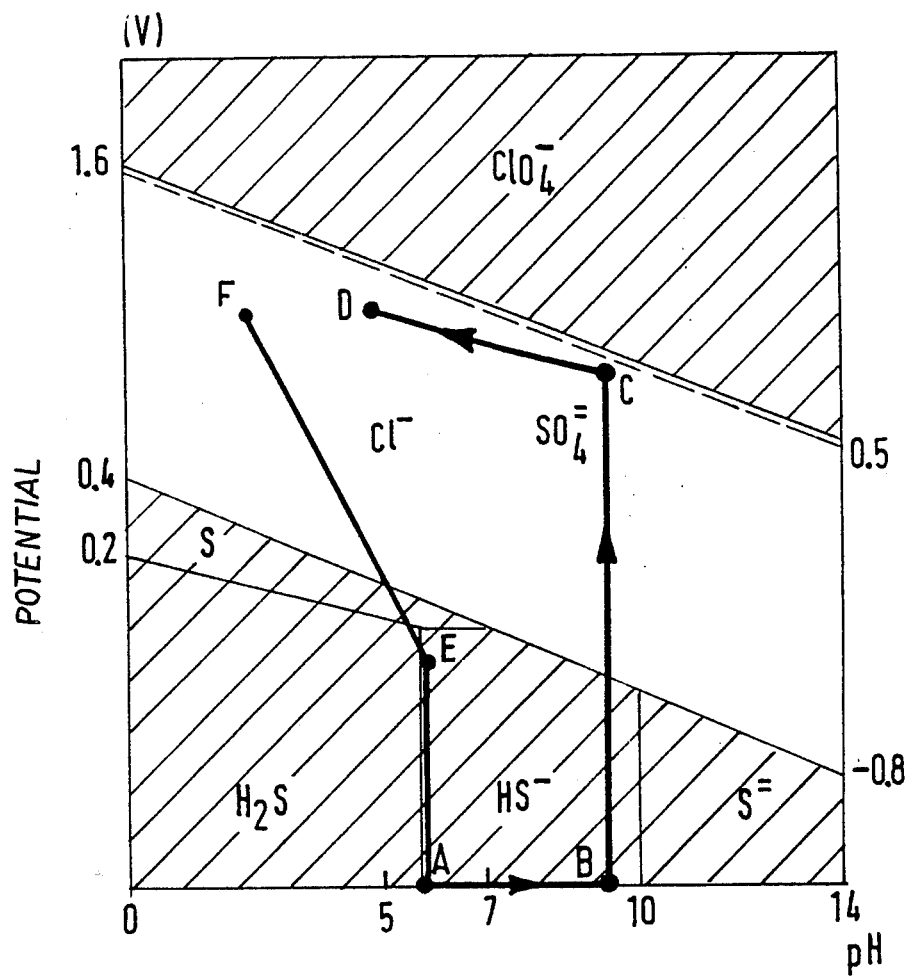

FIG. 1 diagramatically illustrates an example of units for the processing of petroleum up to its distillation and the location of the chloride analyzer in the overhead distillate-vapors circuit;

FIG. 2 shows the diagram of a preferred form of the chloride ion analyzer in accordance with the invention; and FIG. 3 shows the so-called Pourbaix oxidation-reduction potential/pH diagram of the regions of existence of the species $H_2S$, $HS^-$, $S°$, $SO_4^{--}$, $Cl$ and $ClO_4^-$.

Referring to FIG. 1, a crude-petroleum processing circuit comprises a desalter 1 in which the major portion of the hydrolyzable salts of the crude petroleum introduced through the pipe 10 is removed; a heating furnace 2 to which the crude petroleum is conducted through the pipe 11, the pipe 12 permitting the removal of the saline waters; and a column 3 for the atmospheric distillation of the crude petroleum, introduced through the pipe 13.

The overhead vapors leaving the top of the distillation column 3 pass by way of the pipe 14 through a first heat exchanger 4 in which their temperature is lowered sufficiently so that only the heaviest hydrocarbons are able to condense. These are collected in a first overhead drum 5 while the steam, freed of the heaviest hydrocarbons, is conducted through an air cooler 6 by way of the pipe 15.

The heaviest hydrocarbons are collected at 22 at the base of the first overhead drum 5. The condensation water, discharged from the air cooler 6 through the pipe 16, is recovered at the base of a second overhead drum 7 through the pipe 17. The noncondensable gases leave that drum through a pipe 16', and the hydrocarbons through a pipe 16''. The pipe 17 divides into two parallel circuits: Circuit 18a, to which the chloride analyzer 9 in accordance with the invention is connected, and circuit 18b, in which pH measurements are made continuously by means of a pH meter 8. The two circuits are reunited in the pipe 19, the condensation water being sent to a treating unit downstream.

With a view to limiting corrosion throughout this overhead circuit, an injection of ammonia, $NH_3$, is made at 20 to maintain the pH of the condensation water in 7 at a value of about 6. This injection is controlled by the pH measurements provided by the pH analyzer 8. A first injection of corrosion inhibitor at 21, and optionally a second one at 21', make it possible to limit corrosion by the first dew drops which form at the level of the air cooler 6 and which contain a very strong concentration of hydrochloric acid of the order of several hundred ppm. These injections are in addition to a soda injection made at 23 into pipe 11 to effectively fight corrosion.

The continuous monitoring through the analyzer 9 of the chloride content of the overhead condensation waters makes it possible to adjust continuously, rapidly and precisely the rates of injection at 21, and optionally at 21', of corrosion inhibitor and also the injection of soda at 23.

The chloride analyzer 9 in accordance with the invention, shown in FIG. 2, will now be described.

This analyzer 9 comprises a vessel 31 in which the sample delivered by the pipe 18a is introduced. It has two outlet pipes, one of which, 32, in its upper portion, permits the discharge of sample overloaded with hydrocarbons, while the second, 33, in the lower portion of the vessel 31, permits conveying the resulting sampling toward the rear of the analyzer 9.

The vessel 31 is provided at its top with a commercial type of capacitive sensor 34 (for example, an Effector sensor) that is sensitive to hydrocarbons and is connected to the detector 35 which, on the basis of the signal coming from the sensor 34, will actuate, through the relay 36, the valves 37, located in pipe 32, and 37', located in pipe 33, respectively.

When the sensor 34 detects hydrocarbons at the bottom of the vessel 31, the valves 37 and 37' are actuated so as to close off access to the rear of the analyzer and to discharge the sample overloaded with hydrocarbons through the discharge pipe 32. The valves 37 and 37' are returned into their initial position when the sensor 34 no longer detects any hydrocarbons at the bottom of the vessel 31. The water then leaves through the pipe 33 and passes through a pneumatic or electric proportioning pump 39. After the pump 39, the purified water is conducted to the holding tank 42. At the base 43 of that tank, nitrogen is blown in at a predetermined rate to sweep the residual volatile hydrocarbons and the hydrogen sulfide toward the porous member 44 placed at the top of the tank 42. The oxidizing solution and the acidifying solution, stored in the containers 40 and 40', respectively, are pumped by two proportioning pumps 41 and 41', respectively (or optionally by a single proportioning pump with two heads), and then injected into the pipe 45, which carries the insufflated water from the holding tank 42. As will be explained further on, the injection of the acidifying solution is effected after the injection of the oxidizing solution.

The water so treated is conducted through the pipe 45 to the closed electrolytic vessel of the measuring cell 46 comprising a water outlet 47, which rejoins the pipe 19, as shown in FIG. 1, and provided with a specific combined electrode 48, for example, of the type CE 9417 B, marketed by the Orion company. This electrode is connected to an assoiciated electronic unit 49, which processes the electric signal generated by the measuring cell and reconstructs it in the form of information that is directly usable (readout of chloride content) and/or optionally recordable. The chloride content, which is displayed continuously, makes it possible for an operator, or through an automatic control system, to adjust the rates of injection of corrosion inhibitor and of soda.

Shown in FIG. 3 is the existence diagram of the chloride ($Cl^-$, $ClO_4^-$) and sulfide ($S°$, $H_2S$, $HS^-$, $S^{--}$ and $SO_4^{--}$) species as a function of oxidation-reduction potential and pH in accordance with the so-called Pourbaix representation. The abscissa gives the pH, which ranges from 0 to 14, and the ordinate, the potential, which varies from $-1$ to $+2$ volts.

The solid curves which separate the existence regions are the so-called molarity curves, on which the species indicated is at a concentration of 1M. However, since its concentration varies exponentially about its curves as a function of the potential, it may be assumed that the species does not exist beyond that curve.

A first example of a practical application of the procedure in accordance with the invention, starting with an overhead water of about pH 6 and with a reduction potential symbolically represented by point A in the diagram, consists in going to point B, of about pH 9, by adding an alkaline agent, for example, soda, and then moving to C, of about pH 9 and with a potential greater than 0.4 volt, by adding an oxidizing agent, for example, potassium permanganate, and then going back to D, of about pH 5 and with a potential greater than 1.1 volts, by adding an acidifying agent, for example, nitric acid.

With the analyzer described above, the displacement actually is directly from A to C by means of a solution that is simultaneously alkaline and oxidizaing. One skilled in the art from the foregoing teaching will be able to visualize an analyzer comprising three injection devices, including a first one for injection of an alkaline agent, without this amounting to seperate invention, and hence without departing from the scope of the present invention.

This displacement in the aforesaid Pourbaix diagram is of interest mainly because it avoids the region of existence of the free sulfur (S°) species, which, once formed, is stable and will plug the sensitive portion of the electrode, fabricated from sintered silver in this type of combined electrode.

A second example of a practical application of the procedure in accordance with the present invention, starting with the same overhead water of pH 6 and with a reduction potential represented by point A in the diagram as in the preceding example, consists in going to point E with a potential of less than $-0.2$ volt by adding an oxidizing agent such as sodium bromate, and then going to point F of pH 2 and with a potential greater than 0.4 volt by adding an acidifying agent, for example, nitric acid. The presence of nitric acid in the sample increases the oxidizing power of the bromate ions, which makes it possible to avoid the formation of free sulfur in passing through the zone of stabilization of the free sulfur (S°).

The continuous analysis procedure and the analyzer in accordance with the invention thus permit the corrosion of the overhead circuits and condensers to be limited and hence their service life too be extended. They further make it possible to realize substantial economies in the quantities of inhibitors injected into the overhead waters and to avoid the drawbacks of overinjection of soda into the crude petroleum.

We claim:

1. A procedure for the continuous analysis of overhead waters for the content of chloride ions present in a hydrocarbon distillation column, which procedure comprises the following steps:
   drawing a sample of at least a part of the overhead waters for analysis;
   removing hydrocarbons and suspended matter from at least a portion of the sampled waters to yield a partially purified sampling;
   blowing nitrogen into the partially purified sampling to remove hydrogen sulfide and residual hydrocarbons;
   oxidizing $S^{2-}$ or $HS^-$ sulfide ions in the sampling to sulfate ions;
   acidifying the sampling to result in a pH appropriate for obtaining stable ionometry results; and
   finally, measuring by ionometry the content of chloride ions present in the partially purified sampling that is oxidized and acidified;
   the steps between sampling and measuring may be in any order.

2. A procedure according to claim 1, wherein the content of chloride ions present is measured by ionometry by means of a combined electrode in a measuring cell.

3. A procedure according to claim 1, wherein the hydrocarbons and the suspended matter are removed from the sample by filtration through an activated carbon filter.

4. A procedure according to claim 2, wherein the hydrocarbons are separated from the water sample and removed by decantation from a vessel comprising at least one hydrocarbon detector and at least one discharge pipe equipped with a valve electrically connected to said detector for permitting the sampling of the water settled in said vessel to flow to the measuring cell and also for discharging that portion of the sample in said vessel when overloaded with hydrocarbons in excess of a predetermined detectable amount.

5. A procedure according to claim 1, wherein the $S^{--}$ and/or $HS^-$ sulfide ions are oxidized to sulfate ions by injecting into the sampling, at a pH such that the formation of free sulfur is avoided, an oxidizing solution whose oxidizing power is sufficient to oxidize the sulfide ions to sulfate ions at the pH of the sampling but not sufficient to oxidize the chloride ions to chlorate ions.

6. A procedure according to claim 4, wherein the $S^{--}$ and/or $HS^-$ sulfide ions are oxidized to sulfate ions by injecting into the sampling, at a pH such that the formation of free sulfur is avoided, an oxidizing solution whose oxidizing power is sufficient to oxidize the sulfide ions to sulfate ions at the pH of the sampling but not sufficient to oxidize the chloride ions to chlorate ions.

7. A procedure according to claim 5 wherein the oxidizing solution contains at least one salt selected from the group consisting of the bromates, $BrO_3^-$, the chromates, $Cr_2O_7^{2-}$, the permanganates, $MnO_4^-$, and the nitrates, $NO_3^-$, of alkali metals and of alkaline-earth metals.

8. A procedure according to claim 6 wherein the oxidizing solution contains at least one salt selected from the group consisting of the bromates, $BrO_3^-$, the chromates, $Cr_2O_7^{2-}$, the permanganates, $MnO_4^-$, and the nitrates, $NO_3^-$, of alkali metals and of alkaline-earth metals.

9. A procedure according to claim 8, wherein the oxidizing solution further contains an alkaline agent.

10. A procedure according to claim 9, wherein the oxidizing solution is a concentrated aqueous solution of from 0.1M to 5M of potassium permanganate, $KMnO_4$, and of from 0.5 to 2N of soda.

11. A procedure according to claim 10, wherein the oxidizing solution is a concentrated aqueous solution of from 0.5M to 2M of potassium permanganate, $KMnO_4$, and of from 0.5 to 2N of soda.

12. A procedure according to claim 8, wherein the oxidizing solution is a concentrated aqueous solution of from 0.5M to 5M of sodium bromate, $NaBrO_3$.

13. A procedure according to claim 12, wherein the oxidizing solution is a concentrated aqueous solution of from 0.5M to 2M of sodium bromate $NaBrO_3$.

14. A procedure according to claim 1, wherein the sampling is acidified by injection of an acidifying solution of a concentration of from 0.1N to 5N, of at least one strong acid selected from the group consisting of sulfuric acid, nitric acid and the halogen acids, with the exception of hydrochloric acid.

15. A procedure according to claim 8, wherein the partially purified sampling that had nitrogen blown into it for removing hydrogen sulfide and residual hydrocarbons is acidified by injection of an acidifying solution of a concentration of from 0.1N to 5N, of at least one strong acid selected from the group consisting of sulfuric acid, nitric acid and the halogen acids, with the exception of hydrochloric acid.

16. A procedure according to claim 6, wherein the oxidizing solution is injected at a rate from 0.001 to 0.5 times the flow rate of the sampling.

* * * * *